US010792642B2

(12) United States Patent
Zhang et al.

(10) Patent No.: US 10,792,642 B2
(45) Date of Patent: Oct. 6, 2020

(54) CATALYST AND PREPARATION METHOD THEREOF, AND METHOD FOR PREPARING ISOBUTYLENE BY APPLYING THE SAME

(71) Applicants: CHINA PETROLEUM & CHEMICAL CORPORATION, Beijing (CN); Fushun Research Institute of Petroleum and Petrochemicals, SINOPEC CORP., Fushun, Liaoning (CN)

(72) Inventors: Shumei Zhang, Liaoning (CN); Feng Zhou, Liaoning (CN); Kai Qiao, Liaoning (CN); Qingtong Zhai, Liaoning (CN); Chunmei Wang, Liaoning (CN)

(73) Assignees: CHINA PETROLEUM & CHEMICAL CORPORATION, Beijing (CN); Fushun Research Institute of Petroleum and Petrochemicals, SINOPEC CORP., Fushun, Liaoning (CN)

( * ) Notice: Subject to any disclaimer, the term of this patent is extended or adjusted under 35 U.S.C. 154(b) by 646 days.

(21) Appl. No.: 15/531,679

(22) PCT Filed: Nov. 25, 2015

(86) PCT No.: PCT/CN2015/095547
§ 371 (c)(1),
(2) Date: May 30, 2017

(87) PCT Pub. No.: WO2016/086781
PCT Pub. Date: Jun. 9, 2016

(65) Prior Publication Data
US 2017/0333876 A1 Nov. 23, 2017

(30) Foreign Application Priority Data

Dec. 3, 2014 (CN) .......................... 2014 1 0717041
Dec. 3, 2014 (CN) .......................... 2014 1 0717045

(51) Int. Cl.
*B01J 21/00* (2006.01)
*B01J 21/12* (2006.01)
*B01J 37/02* (2006.01)
*C07C 1/24* (2006.01)
*C07C 1/20* (2006.01)
*B01J 35/00* (2006.01)
*C07C 11/09* (2006.01)

(52) U.S. Cl.
CPC .............. *B01J 21/12* (2013.01); *B01J 35/00* (2013.01); *B01J 35/0006* (2013.01); *B01J 37/02* (2013.01); *C07C 1/20* (2013.01); *C07C 1/24* (2013.01); *C07C 11/09* (2013.01)

(58) Field of Classification Search
CPC ........ B01J 21/12; B01J 35/00; B01J 35/0006; B01J 37/02; B01J 37/08; B01J 37/0215; B01J 35/1019; B01J 35/023; B01J 35/0073; B01J 21/04; C07C 11/09; C07C 1/20; C07C 1/24
USPC ......................................................... 502/232
See application file for complete search history.

(56) References Cited

U.S. PATENT DOCUMENTS

| | | | |
|---|---|---|---|
| 3,665,048 A | 5/1972 | Grane et al. | |
| 4,254,290 A | 3/1981 | Chambers et al. | |
| 4,423,271 A | 12/1983 | Obenaus et al. | |
| 4,447,668 A | 5/1984 | Smith, Jr. et al. | |
| 4,551,567 A | 11/1985 | Smith, Jr. | |
| 4,570,026 A | 2/1986 | Keyworth et al. | |
| 5,179,054 A * | 1/1993 | Schipper | B01J 33/00 502/65 |
| 5,880,324 A | 3/1999 | de Agudelo et al. | |
| 2005/0014985 A1 | 1/2005 | Grund et al. | |

(Continued)

FOREIGN PATENT DOCUMENTS

| | | |
|---|---|---|
| CN | 1185992 A | 7/1998 |
| CN | 1853772 A | 11/2006 |
| CN | 101300211 A | 11/2008 |

(Continued)

OTHER PUBLICATIONS

Asmatulu, R.. (2002). Removal of the discoloring contaminants of an East Georgia kaolin clay and its dewatering. Env. Sci. 26. 447-453. (Year: 2002).*

*Primary Examiner* — Haytham Soliman
(74) *Attorney, Agent, or Firm* — Novick, Kim & Lee, PLLC; Allen Xue

(57) ABSTRACT

The present invention relates to the field of isobutylene preparation. Disclosed are a catalyst and preparation method thereof, and method for preparing isobutylene by applying the same; the catalyst has a core-shell structure, the core an amorphous silica-alumina particle and/or an aggregate molding thereof, and the shell aluminum oxide comprising silicon and tin; the weight ratio of aluminum oxide comprising silicon and tin to amorphous silica-alumina is 1:60-1:3; in the aluminum oxide comprising silicon and tin, on basis of the weight of aluminum oxide comprising silicon and tin, the content of silicon is 0.5-2 wt %, and of tin is 0.2-1 wt %. The catalyst of the present invention is used to catalyze a mixture of MTBE and TBA to prepare isobutylene, enabling the MTBE cleavage and TBA dehydration reactions to be conducted simultaneously to generate isobutylene, achieving higher conversion rates of TBA and MTBE, and higher selectivity for generating isobutylene.

26 Claims, No Drawings

(56) References Cited

U.S. PATENT DOCUMENTS

2009/0178955 A1    7/2009   Ryu

FOREIGN PATENT DOCUMENTS

| | | |
|---|---|---|
| CN | 101486622 A | 7/2009 |
| CN | 102451674 A | 5/2012 |
| CN | 102516030 A | 6/2012 |
| CN | 103506158 A | 1/2014 |
| CN | 103611572 A | 3/2014 |
| DE | 3210435 A1 | 10/1982 |
| EP | 0118085 A1 | 9/1984 |
| EP | 0198236 A2 | 10/1986 |
| FR | 2894975 A1 | 12/2006 |
| GB | 1482883 A | 8/1977 |
| JP | 49-094602 A | 9/1974 |
| JP | 51-026401 B | 8/1976 |
| JP | 3220136 B2 | 10/2001 |
| JP | 2002320857 A | 11/2002 |
| JP | 2003505539 A | 2/2003 |
| JP | 2004091443 A | 3/2004 |
| JP | 2004115407 A | 4/2004 |
| JP | 2008055420 A | 3/2008 |
| JP | 2012045516 A | 3/2012 |
| WO | 2009022544 A1 | 2/2009 |

\* cited by examiner

CATALYST AND PREPARATION METHOD THEREOF, AND METHOD FOR PREPARING ISOBUTYLENE BY APPLYING THE SAME

FIELD OF THE INVENTION

The present invention relates to the preparation of isobutylene, in particular to a catalyst, a preparation method of a catalyst and a catalyst prepared by the method, a use of the catalyst, and a method for preparing isobutylene by applying the catalyst.

BACKGROUND OF THE INVENTION

Isobutylene is an important organic chemical raw material, and is mainly used to produce fine chemical products such as methyl methacrylate (MMA), butyl rubber, polyisobutylene, tert-butylphenol, tert-butylamine, methallyl chloride, trimethylacetic acid, isoprene, p-tert-octylphenol, anti-oxidants, intermediates of pesticides and medicines, tert-butyl acetate, and silicane, etc. The raw materials for producing isobutylene are mainly from C4 fraction byproducts obtained in installation for producing ethylene from naphtha by steam cracking, C4 fraction byproducts obtained in fluid catalytic cracking (FCC) installations in oil refineries, and tert-butyl alcohol byproduct obtained in propylene oxide synthesis through a Halcon process, etc., wherein, the industrial processes for producing isobutylene mainly include sulfuric acid extraction process, adsorptive separation process, tert-butyl alcohol dehydration process, methyl tert-butyl ether cracking process, and n-butylene isomerization process, etc. The MTBE cracking process is a process that is advanced in technology and has higher economic efficiency among the isobutylene preparation processes. In the reaction process of MTBE cracking for isobutylene, the main reaction is MTBE cracking into isobutylene and methanol under the action of a catalyst; finally, isobutylene or high-purity isobutylene is obtained through procedures such as rectification, etc. There are a variety of catalysts that can be used in MTBE cracking for isobutylene, including aluminum oxide, silicon oxide, amorphous silica-alumina, ion exchange resin, molecular sieve, solid phosphoric acid, and other acidic catalyst systems. For example, the catalysts for MTBE cracking for isobutylene disclosed in patent documents CN1853772A, CN102451674A, JP2004115407, JP2004091443, and JP3220136, etc. are amorphous silica-alumina catalysts; in patent documents DE3509292, DE3210435, U.S. Pat. No. 4,447,668, GB1482883, U.S. Pat. No. 4570026, U.S. Pat. No. 4551567, etc., ion exchange resin catalysts are used; in patent documents CN96123535.7, EP0118085, JP7626401, and JP7494602, etc., solid phosphoric acid, sulfate, or active carbon is used as a MTBE cracking catalyst.

Another common method for preparing isobutylene is TBA dehydration. The reaction of TBA dehydration for preparing isobutylene has advantages including less byproduct, easy separation and refinement, and low investment, etc. Common catalysts include aluminum oxide, molecular sieve, and sulfonic acid ion exchange resin, etc. For example, the isobutylene dehydration catalysts disclosed in patent documents U.S. Pat. No. 3665048, CN101300211A, and CN102516030A, etc. are aluminum oxide catalysts. In patent documents U.S. Pat. No. 4423271 and U.S. Pat. No. 2005/0014985A1, etc., sulfonic acid resin is used as a catalyst. The catalyst for tert-butyl alcohol cracking reaction provided in patent documents CN103611572A and CN103506158A is prepared with the following method: mixing polystyrene, chlorinated polyvinyl chloride, polytrifluorochloroethylene, and polyvinylidene fluoride or polytribromostyrene, melting and pelleting the mixture, and controlling the pellet product to have a sulfonation reaction with sulfuric anhydride, so as to obtain the catalyst.

In the production process, a mixture of MTBE and TBA is often obtained, usually TBA is co-produced in the preparation of MTBE. Firstly, there are some technical difficulties specialized in producing TBA. The TBA production process is complex; the concentration of TBA product is only 45%-55% owing to the poor mutual solubility between C4 fractions and water; TBA at 85% concentration can only be obtained through conventional rectification because TBA is azeotropic with water and difficult to separate from water. Usually, a TBA product at a higher concentration can be obtained only through multiple stages of extraction and rectification, but the equipment investment and the operation cost are severely increased. Secondly, co-producing TBA in the preparation of MTBE has technical advantages: (1) the scheme is simple and flexible. The process scheme can be adjusted appropriately according to the market demand for the product.

MTBE or TBA can be produced separately, or a mixture of MTBE and TBA can be produced, simply by switching the process flow and replacing the catalyst with an appropriate catalyst. (2) The process is easy to implement, and the investment risk is low. The separate MTBE production process can be renovated easily into a co-production process, which is easy to implement. In addition, the conventional separate production process can be recovered conveniently, and the spare MTBE/TBA separating tower can be used to separate n-butylene from C4 fractions. Therefore, that technique involves no investment risk. Finally, the investment cost of the co-production installation is low. In contrast, if the manufacturer employs specialized separate MTBE production installations and specialized separate TBA production installations, which are independent from each other and can't share equipment between each other, more equipment units will be required, and the investment will be higher. A combined production installation can be used to produce MTBE and TBA at the same time; thus, compared with two sets of separate installations at the same scale for producing MTBE and TBA separately, the investment can be reduced by 40% or more, and the operation cost can be greatly reduced too. Hence, the techniques for co-producing TBA in the preparation of MTBE have received extensive attention. Chunlong Lu from Xi'an Shiyou University has analyzed the techniques of co-producing TBA in the preparation of MTBE seriously and obtained a positive answer in his magisterial thesis "Optimization Analysis of MTBE Installations and Primary Exploration of Combined Production of MTBE and TBA".

At present, when a mixture of MTBE and TBA obtained through combined production is used to prepare isobutylene, usually the mixture is separated to obtain pure MTBE raw material and TBA raw material, and then the pure MTBE raw material and TBA raw material are used respectively in a MTBE cracking installation and a TBA dehydration installation to prepare isobutylene respectively.

There is no technique for preparing isobutylene from a mixture of MTBE and TBA by cracking in the present stage. A major reason is that a MTBE cracking installation and a TBA dehydration installation are different from each other in terms of the requirement for catalyst performance. Usually, the active sites on the surface of the MTBE cracking catalyst are mainly Bronsted acid (B-acid) sites, while the catalyst for preparing isobutylene through TBA dehydration undergoes a catalyzed reaction process of Lewis acid (L-acid). A single catalyst may mainly consist of B-acid or L-acid, but not both. Another reason is that the reaction conditions required by the catalysts, especially the reaction temperatures, are different; specifically, the TBA dehydration temperature (usually 260° C.-300° C.) is higher than the MTBE cracking temperature (usually 200° C.-230° C.); if the temperature is lower that the value specified above, the conversion rate will be decreased severely; if the reaction temperature is higher than the value specified above, more byproducts will be produced, causing degraded selectivity for isobutylene. Generally, isobutylene products with purity higher than 99.5% (high-purity isobutylene) are in a higher demand, applied more widely, and have a higher industrial production value. Therefore, how to prepare isobutylene from a mixture of MTBE and TBA in the same apparatus under the same reaction conditions while maintaining high activity and selectivity is an important research subject in the art.

SUMMARY OF THE INVENTION

To overcome the above-mentioned drawbacks in the prior art, the present invention provides a catalyst, a preparation method of a catalyst, a catalyst prepared by the method, a use of the catalyst in isobutylene preparation, and a method for preparing isobutylene by applying the catalyst. When the catalyst of the present invention is used to catalyze a mixture of MTBE and TBA to prepare isobutylene, a MTBE cracking reaction and a TBA dehydration reaction can be executed simultaneously to produce isobutylene, achieving higher conversion rates of TBA and MTBE and higher selectivity for generating isobutylene.

To attain the objects described above, in a first aspect, the present invention provides a catalyst having a core-shell structure, the core being an amorphous silica-alumina particle and/or a particle aggregate, and the shell being aluminum oxide containing silicon and tin, the weight ratio of the aluminum oxide containing silicon and tin to the amorphous silica-alumina is 1:60-1:3, preferably is 1:40-1:4, further preferably is 1:30-1:6; in the aluminum oxide containing silicon and tin, on the basis of the weight of the aluminum oxide containing silicon and tin and calculated as elements, the content of silicon is 0.5-2 wt %, preferably is 0.8-1.5 wt %, and the content of tin is 0.2-1 wt %, preferably is 0.3-0.8 wt %.

In a second aspect, the present invention provides a preparation method of a catalyst, comprising: mixing a silicon-containing compound, a tin-containing compound, and aluminum hydroxide slurry to obtain an aluminum hydroxide slurry containing silicon and tin, spraying the aluminum hydroxide slurry containing silicon and tin on amorphous silica-alumina particles and/or particle aggregates, and then drying and calcining the resultants sequentially.

In a third aspect, the present invention provides a catalyst prepared by the above-mentioned method.

In a fourth aspect, the present invention provides a use of the above-mentioned catalyst of the present invention in MTBE cracking reaction for preparing isobutylene and/or TBA dehydration reaction for preparing isobutylene.

In a fifth aspect, the present invention provides a method for preparing isobutylene, comprising: contacting the above-mentioned catalyst of the present invention with MTBE and/or TBA for reaction to prepare isobutylene.

The catalyst of the present invention is a novel catalyst, which employs aluminum oxide containing silicon and tin (modified aluminum oxide) as a shell, and employs or mainly employs amorphous silica-alumina as a core; the shell and the core cooperate with each other closely, so that a MTBE cracking reaction and a TBA dehydration reaction can be executed simultaneously to prepare isobutylene, achieving higher conversion rates of TBA (99.0% or higher) and MTBE (99.0% or higher) and higher selectivity for generating isobutylene (99.5% or higher).

In the preparation method of a catalyst according to the present invention, a silicon-containing compound and a tin-containing compound are introduced into an aluminum hydroxide slurry, amorphous silica-alumina particles and/or particle aggregates are sprayed with the aluminum hydroxide slurry containing silicon and tin, so that the catalyst obtains a uniform and stable core-shell structure, and the core and the shell are coupled more tightly.

When the catalyst of the present invention is used in the reactions for preparing isobutylene from a mixture of MTBE and TBA, a TBA dehydration reaction and a MTBE cracking reaction can be executed simultaneously to prepare isobutylene; thus, a separation process of the mixture of MTBE and TBA is avoided, it is unnecessary to construct a MTBE cracking installation and a TBA dehydration installation separately to prepare isobutylene, the operation steps and investment are reduced, and higher conversion rates of TBA (99.0% or higher) and MTBE (99.0% or higher) and higher selectivity for generating isobutylene (99.5% or higher) are achieved. Other features and advantages of the present invention will be further detailed in the embodiments hereunder.

DETAILED DESCRIPTION OF THE EMBODIMENTS

Hereunder some embodiments of the present invention will be detailed. It should be appreciated that the embodiments described here are only provided to describe and explain the present invention, but shall not be deemed as constituting any limitation to the present invention. In a first aspect, the present invention provides a catalyst having a core-shell structure, the core being an amorphous silica-alumina particle and/or a particle aggregate, and the shell being aluminum oxide containing silicon and tin, the weight ratio of the aluminum oxide containing silicon and tin to the amorphous silica-alumina is 1:60-1:3; in the aluminum oxide containing silicon and tin, on the basis of the weight of the aluminum oxide containing silicon and tin and calculated as elements, the content of silicon is 0.5-2 wt %, and the content of tin is 0.2-1 wt %. Those skilled in the art should appreciate: the catalyst of the present invention is a catalyst that has a core-shell structure in which the core is an amorphous silica-alumina particle and/or a particle aggregate, and the shell is aluminum oxide containing silicon and tin, but is not limited to catalysts that have a core-shell structure in which the core solely consists of an amorphous silica-alumina particle and the shell solely consists of aluminum oxide containing silicon and tin; for example, the core may further contain a binder described in the following text, or the shell may further contain a binder described in the following text.

Those skilled in the art should appreciate: in the catalyst of the present invention, the active sites on the surface of the amorphous silica-alumina particle and/or particle aggregate that serves as a component of the core structure are mainly B-acid sites for catalyzing the MTBE cracking reaction to prepare isobutylene; the active sites on the surface of the aluminum oxide containing silicon and tin that serves as a component of the shell structure are mainly L-acid sites for catalyzing the TBA dehydration reaction to prepare isobutylene. On the premise of enabling simultaneous MTBE cracking reaction and TBA dehydration reaction to prepare isobutylene, to ensure a stable core-shell structure of the catalyst of the present invention and make the catalyst structure more uniform and the core-shell coupling tighter, the weight ratio of the aluminum oxide containing silicon and tin to the amorphous silica-alumina is controlled within a range of 1:60-1:3. When a mixture of MTBE and TBA is used as a raw material to prepare isobutylene with the catalyst of the present invention, the weight ratio of the aluminum oxide containing silicon and tin to the amorphous silica-alumina in the catalyst of the present invention may be adjusted appropriately according to the weight ratio of MTBE to TBA in the mixture. For example, if the content of MTBE is relatively high in the mixture, the amount of the amorphous silica-alumina may be increased appropriately within the range of weight ratio of aluminum oxide containing silicon and tin to amorphous silica-alumina (1:60-1:3); in contrast, if the content of TBA is relatively high in the mixture, the amount of the aluminum oxide containing silicon and tin may be increased appropriately within the range of weight ratio of aluminum oxide containing silicon and tin to amorphous silica-alumina (1:60-1:3).

In the catalyst of the present invention, to further stabilize the core-shell structure of the catalyst and make the catalyst structure more uniform and the core-shell coupling tighter, preferably, the weight ratio of the aluminum oxide containing silicon and tin to the amorphous silica-alumina is 1:40-1:4, further preferably is 1:30-1:6.

In the catalyst of the present invention, to further improve the conversion rate of TBA and the selectivity for generating isobutylene with the catalyst, preferably, on the basis of the weight of the aluminum oxide containing silicon and tin and calculated as elements, the content of silicon is 0.8-1.5 wt %, and the content of tin is 0.3-0.8 wt %.

In the present invention, the silicon and tin elements are evenly distributed in the aluminum oxide. As described above, the content of silicon is 0.5-2 wt %, preferably is 0.8-1.5 wt %, and the content of tin is 0.2-1 wt %, preferably is 0.3-0.8 wt %, which means, when the contents of silicon and tin elements are measured with an ICP method with the shell of the same catalyst particle at any position, the contents of silicon and tin elements measured at each position are within the above-mentioned content ranges, and the content of silicon measured at each position meets: (measured value−average value)/average value≤5%, and the content of tin measured at each position meets: (measured value−average value)/average value≤10%. Wherein, the average value is the average of the element content values measured at different positions. To fully demonstrate that the silicon and tin elements are evenly distributed in the aluminum oxide in the catalyst of the present invention, measurements are made at 20 points in the present invention, and the 20 points are grouped into three groups according to the depth to the core: group A consists of 10 points evenly dispersed along the circumference of the shell layer (i.e., on a surface at depth to the core equal to 100% thickness of the shell layer), group B consists of 5 points evenly dispersed in a tangent plane at depth to the core equal to 50% thickness of the shell layer (i.e., on a surface formed by removing the shell by 50% thickness), and group C consists of 5 points evenly dispersed in a tangent plane at depth to the core equal to 10% thickness of the shell layer (i.e., on a surface formed by removing the shell by 90% thickness).

In the catalyst of the present invention, to further stabilize the core-shell structure of the catalyst and make the catalyst structure more uniform and the core-shell coupling tighter, preferably, the ratio of the size of the core to the thickness of the shell is 200:0.5-200:20, further preferably is 200:0.6-200:15, still further preferably is 200:1.2-200:6.

In the catalyst of the present invention, to further stabilize the core-shell structure of the catalyst and make the catalyst structure more uniform and the core-shell coupling tighter, preferably, the thickness of the shell is 3-300 μm, further preferably is 5-280 μm, still further preferably is 5-260 μm. Furthermore, if the core is an amorphous silica-alumina particle, the thickness of the shell is 3-15 μm, preferably is 5-10 μm, further preferably is 5-8 μm; if the core is a particle aggregate, the thickness of the shell is 5-300 μm, preferably is 8-280 μm, further preferably is 10-260 μm.

In the present invention, the particle aggregate refers to an aggregate consisting of a plurality of amorphous particles, which is obtained by molding the amorphous silica-alumina particles with a binder. A catalyst product obtained by loading particle aggregates with aluminum oxide containing silicon and tin corresponds to the molded catalyst product obtained by carrying out catalyst molding before spraying the aluminum hydroxide slurry containing silicon and tin on the amorphous silica-alumina, as described below.

In the present invention, the thickness of the shell, the size of the catalyst, and the size of the core are obtained by SEM, wherein, the size refers to maximum particle size; specifically, for spherical particles, the size refers to particle diameter.

To further stabilize the core-shell structure of the catalyst, make the catalyst structure more uniform and the core-shell coupling tighter, and further improve the conversion rate of MTBE and selectivity for generating isobutylene with the catalyst, preferably, in the core, on the basis of the weight of the amorphous silica-alumina, the content of silicon calculated in $SiO_2$ is 60-99 wt %, further preferably is 70-95 wt %, still further preferably is 80-92 wt %; the content of aluminum calculated in $Al_2O_3$ is 1-40 wt %, further preferably is 5-30 wt %, still further preferably is 7-20 wt %. Those skilled in the art should appreciate: in the catalyst of the present invention, the amorphous silica-alumina refers to amorphous aluminum silicate, which is usually obtained by calcining silica-alumina gel and mainly contains aluminum silicate, the content of silicon calculated in $SiO_2$ and the content of aluminum calculated in $Al_2O_3$ described above only represent the contents of silicon and aluminum elements in the amorphous silica-alumina, rather than indicating that the silicon is in the form of silicon oxide and the aluminum is in the form of aluminum oxide.

In the catalyst of the present invention, to further stabilize the core-shell structure of the catalyst, make the catalyst structure more uniform and the core-shell coupling tighter, and further improve the conversion rate of MTBE and selectivity for generating isobutylene with the catalyst, preferably, the amorphous silica-alumina has the following properties: specific surface area of 240-450 $m^2/g$, preferably 270-410 $m^2/g$; pore volume of 0.4-0.9 mL/g, preferably 0.5-0.7 mL/g.

In the catalyst of the present invention, there is no particular restriction on the preparation method of the amorphous silica-alumina; in other words, the amorphous silica-alumina may be prepared with any conventional method in the art, such as co-precipitation method, fractional precipitation method, or mechanical mixing method. The inventor of the present invention has further found in the research: if the amorphous silica-alumina is treated by hydrothermal treatment at 150-450° C. for 5-24 h, the quantity of B-acid sites on the surface of the amorphous silica-alumina can be significantly increased while the quantity of L-acid sites can be significantly reduced, and the pore size of the amorphous silica-alumina can be increased; thus, the conversion rate of MTBE and selectivity for generating isobutylene can be further improved with the catalyst. Therefore, to further improve the conversion rate of MTBE and selectivity for generating isobutylene with the catalyst, preferably, the amorphous silica-alumina is obtained through hydrothermal treatment, and the conditions of the hydrothermal treatment include: temperature of 150-450° C., time of 5-24 h. Further preferably, the amorphous silica-alumina is amorphous silica-alumina obtained through saturated water vapor treatment controlled under the above temperature and time conditions. After the hydrothermal treatment, the properties of the amorphous silica-alumina, such as the quantity of B-acid sites and pore size, etc., are changed obviously.

The inventor of the present invention has further found in the research: in the catalyst of the present invention, if the amorphous silica-alumina further contains an activator that is selected from one or more of Family IIA metal elements and Family VIII metal elements, besides silicon and aluminum elements, the conversion rate of MTBE and selectivity for generating isobutylene with the catalyst can be further improved. Therefore, to further improve the conversion rate of MTBE and selectivity for generating isobutylene with the catalyst, preferably, besides silicon and aluminum elements, the amorphous silica-alumina further contains an activator selected from one or more of Family IIA metal elements and Family VIII metal elements; in the activator-containing amorphous silica-alumina, on the basis of the weight of the activator-containing amorphous silica-alumina, the content of the activator calculated in oxide is 0.1-5 wt %. Those skilled in the art should appreciate: the activator oxide means that the activator exists in the form of a stable oxide in the amorphous silica-alumina, i.e., exists in the form of a stable oxide of the Family IIA metal elements or VIII Family metal elements. Further preferably, the Family IIA metal elements are one or more of Be, Mg and Ca, and the Family VIII metal elements are one or more of Ni, Pd and Pt.

In the catalyst of the present invention, to further stabilize the core-shell structure of the catalyst, make the catalyst structure more uniform and the core-shell coupling tighter, and further improve the conversion rate of MTBE and selectivity for generating isobutylene with the catalyst, preferably, on the basis of the weight of the activator-containing amorphous silica-alumina, the content of silicon calculated in $SiO_2$ is 60-99 wt %, further preferably is 70-95 wt %, still further preferably is 80-92 wt %; the content of aluminum calculated in $Al_2O_3$ is 1-40 wt %, further preferably is 5-30 wt %, still further preferably is 7-20 wt %; the content of the activator calculated in oxide is 0.1-5 wt %, further preferably is 0.3-2 wt %, still further preferably is 0.5-1.5 wt %.

The catalyst of the present invention may be a molded catalyst or non-molded catalyst, which may be selected by those skilled in the art according to the specific process in the actual application, which is well known to those skilled in the art. For example, if the catalyst is used in a fixed bed-type reactor, usually the catalyst is manufactured into a molded catalyst. The molded catalyst may be manufactured into appropriate size and shape, such as spherical shape or strip shape, etc., according to the actual circumstance. Preferably, the catalyst is a molded catalyst, i.e., the catalyst further contains a binder. Further preferably, the particle aggregate contains amorphous silica-alumina and a binder; or, the core is an amorphous silica-alumina particle, and the catalyst further contains a binder. There is no particular restriction on the binder; in other words, the binder may be any conventional binder in the art. Preferably, the binder is microporous alumina; further preferably, the pore size of the microporous alumina is 0.8-2.5 nm. Preferably, with respect to 100 pbw (part by weight) amorphous silica-alumina particles, the amount of the binder is 3-20 pbw, further preferably is 5-10 pbw.

In the catalyst of the present invention, preferably, the catalyst is in a spherical shape, and the diameter of the spherical catalyst is 1-5 mm, preferably is 2-5 mm.

The core-shell structure of the catalyst in the present invention may be confirmed by TEM observation, electron diffraction analysis, and elementary composition analysis, etc., and the compositions of the core and shell may be measured.

In a second aspect, the present invention provides a preparation method of a catalyst, comprising: mixing a silicon-containing compound, a tin-containing compound, and aluminum hydroxide slurry to obtain an aluminum hydroxide slurry containing silicon and tin, spraying the aluminum hydroxide slurry containing silicon and tin on amorphous silica-alumina particles and/or particle aggregates, and then drying and calcining the resultants sequentially.

In the method according to the present invention, preferably, the quantities of the silicon-containing compound, tin-containing compound, and aluminum hydroxide slurry are controlled, so that on the basis of the weight of the aluminum oxide containing silicon and tin in the obtained catalyst, the content of silicon is 0.5-2 wt %, further preferably is 0.8-1.5 wt %, and the content of tin is 0.2-1 wt %, further preferably is 0.3-0.8 wt % (i.e., in the aluminum oxide containing silicon and tin, on the basis of the weight of the aluminum oxide containing silicon and tin, the content of silicon is 0.5-2 wt %, further preferably is 0.8-1.5 wt %, and the content of tin is 0.2-1 wt %, further preferably is 0.3-0.8 wt %); the quantities of the aluminum hydroxide slurry containing silicon and tin and the amorphous silica-alumina particles and/or particle aggregates are controlled, so that the weight ratio of the aluminum oxide containing silicon and tin to the amorphous silica-alumina in the obtained catalyst is 1:60-1:3, further preferably is 1:40-1:4, still further preferably is 1:30-1:6.

In the method according to the present invention, preferably, the quantities of the aluminum hydroxide slurry containing silicon and tin and the amorphous silica-alumina particles and/or particle aggregates are controlled, so that the thickness of the shell in the obtained catalyst is 3-300 μm, further preferably is 5-280 pm, still further preferably is 5-260 μm. Furthermore, if the core is an amorphous silica-alumina particle, the thickness of the shell is 3-15 μm, preferably is 5-10 μm, further preferably is 5-8 μm; if the core is a particle aggregate, the thickness of the shell is 5-300 μm, preferably is 8-280 μm, further preferably is 10-260 μm.

In the method according to the present invention, preferably, the quantities of the aluminum hydroxide slurry containing silicon and tin and the amorphous silica-alumina particles and/or particle aggregates are controlled, so that the ratio of the size of the core to the thickness of the shell in the obtained catalyst is 200:0.5-200:20, preferably is 200:0.6-200:15, further preferably is 200:1.2-200:6.

In the present invention, the spraying and immersion is a common technical means in the catalyst preparation field, and the apparatus and operating method for the spraying may be selected with reference to the prior art, and will not be detailed further here.

In the method according to the present invention, preferably, the method for mixing the silicon-containing compound, tin-containing compound, and aluminum hydroxide slurry comprises: adding the silicon-containing compound and tin-containing compound in batches or in droplets into the aluminum hydroxide slurry while stirring. Those skilled in the art should appreciate: the silicon-containing compound and tin-containing compound should be added slowly, to prevent from any safety hazard incurred by rapid heat release.

In the method according to the present invention, preferably, the amorphous silica-alumina is obtained through hydrothermal treatment, i.e., preferably, the method according to the present invention further comprises treating the amorphous silica-alumina product by hydrothermal treatment before spraying the aluminum hydroxide slurry containing silicon and tin on the amorphous silica-alumina or immersing the amorphous silica-alumina in the aluminum hydroxide slurry containing silicon and tin. The conditions of the hydrothermal treatment include: temperature of 150-450° C., preferably 180-350° C.; time of 5-24 h, preferably 8-16 h.

In the method according to the present invention, preferably, besides silicon and aluminum elements, the amorphous silica-alumina further contains an activator, which is selected from one or more of Family IIA metal elements and Family VIII metal elements, and, on the basis of the weight of the activator-containing amorphous silica-alumina, the content of the activator calculated in oxide is 0.1-5 wt %. Further preferably, the Family IIA metal elements are one or more of Be, Mg and Ca, and the Family VIII metal elements are one or more of Ni, Pd and Pt. In the method according to the present invention, the activator component may be loaded before or after hydrothermal treatment with saturated water vapor, so as to obtain activator-containing amorphous silica-alumina. There is no particular restriction on the loading method; in other words, the loading method can be any method that can be conceived by those skilled in the art; for example, the loading method may be an immersion method, and the specific process may be as follows: immersing amorphous silica-alumina in a water solution of dissoluble inorganic salt that contains an activator, wherein, calculated in the activator, the concentration of the water solution of dissoluble inorganic salt that contains the activator is 0.08-2.0 mol/L; then, calcining the amorphous silica-alumina at 200-600° C. for 3-8 h after immersing.

In the method according to the present invention, the properties of the amorphous silica-alumina, such as the contents of silicon, aluminum and activator, specific surface area, and pore volume, etc., may be determined with reference to the description above, and will not be further detailed here.

In the method according to the present invention, the aluminum hydroxide slurry is usually pseudo-boehmite slurry. Pseudo-boehmiteis also known as monohydrate alumina or false water boehmite, the molecular formula of pseudo-boehmite is $AlOOH \cdot nH_2O$ (n=0.08-0.62). There is no particular restriction on the preparation method of the aluminum hydroxide slurry; in other words, any conventional method in the art may be used. For example, aluminum alkoxide hydrolysis, acid or alkali dissolution of aluminum salt or aluminate, or carbonization by charging $CO_2$ into $NaAlO_2$ solution, etc., may be used. The specific operating methods are well known to those skilled in the art, and will not be further detailed here.

In the method according to the present invention, there is no particular restriction on the silicon-containing compound; in other words, the silicon-containing compound may be any common water-soluble or hydrolyzable silicon-containing compound that may be used as a silicon source in the art; preferably, the silicon-containing compound is one or more of chlorosilane and polyether modified silicon oil. Wherein, the inventor of the present invention has further found in the research: when chlorosilane is added into the aluminum hydroxide slurry, the chlorosilane and the tin-containing compound are hydrolyzed separately, so that suitable active sites for TBA dehydration reaction are provided for the aluminum oxide in the shell layer; moreover, the existence of silicon and other groups (including organic groups and acidic groups, etc.) is beneficial for improving the distribution of pore canals in the shell layer of the catalyst and the connectivity between the pore canals in the shell layer and the pore canals in the core layer, helpful for the mixture to react and quickly diffuse to the core layer. In addition, the acids (including hydrochloric acid, etc.) generated during the hydrolysis of the chlorosilane and the tin-containing compound are helpful for increasing the viscosity of the slurry, so that the catalyst structure is more uniform, and the core-shell coupling is tighter. Therefore, further preferably, the silicon-containing compound is chlorosilane. Wherein, the chlorosilane preferably is hydrolysable chlorosilane; for example, the chlorosilane may be monochlorosilane, dichlorosilane, or chlorosilane that contains two or more chlorine atoms, such as alkyl chlorosilane or alkoxychlorosilane, wherein, preferably the carbon numbers of alkyl and alkoxy are 1-7 respectively. Specifically, the chlorosilane is one or more of dimethyl dichlorosilane, trimethylchlorosilane, and phenyl chlorosilane, wherein, the added amount of chlorosilane (calculated in silicon) is 0.5-2 wt % of aluminum hydroxide (calculated in aluminum oxide), preferably is 0.8-1.5 wt %.

In the method according to the present invention, preferably, the tin-containing compound is hydrolyzable tin-containing compound or water-soluble tin-containing compound; specifically, the tin-containing compound is one or more of tin dichloride, tin tetrachloride, tin nitrate, tin sulfate, tin octoate, and dibutyl tin dichloride, wherein, the added amount of tin-containing compound (calculated in tin) is 0.2-1 wt % of aluminum hydroxide (calculated in aluminum oxide), preferably is 0.3-0.8 wt %.

In the method according to the present invention, the quantities of the aluminum hydroxide slurry containing silicon and tin and the amorphous silica-alumina particles and/or particle aggregates used in the spraying may be determined with reference to the above description in the section related with the catalyst, so that the weight ratio of the aluminum oxide containing silicon and tin to the amorphous silica-alumina in the obtained catalyst is 1:60-1:3, preferably is 1:40-1:4, further preferably is 1:30-1:6; the thickness of the shell is 3-300 μm, further preferably is 5-280 μm, still further preferably is 5-260 μm. Furthermore, if the core is an amorphous silica-alumina particle, the thickness of the shell is 3-15 μm, preferably is 5-10 μm, further preferably is 5-8 μm; if the core is a particle aggregate, the thickness of the shell is 5-300 μm, preferably is 8-280 μm, further preferably is 10-260 μm. The ratio of the size of the core to the thickness of the shell may be 200:0.5-200:20, preferably is 200:0.6-200:15, further preferably is 200:1.2-200:6.

In the method according to the present invention, the catalyst may be a molded catalyst or non-molded catalyst, which can be selected according to the specific process in the actual application. Preferably, the catalyst is a molded catalyst; the molding of the catalyst comprises: spraying the aluminum hydroxide slurry containing silicon and tin on the amorphous silica-alumina particles or immersing the amorphous silica-alumina particles in the aluminum hydroxide slurry containing silicon and tin, and then molding the catalyst.

In the method according to the present invention, preferably, the particle aggregates are obtained by molding amorphous silica-alumina particles, spraying the aluminum hydroxide slurry containing silicon and tin on the amorphous silica-alumina particles, and then drying and calcining the resultants.

In the present invention, preferably, the molding is carried out by bonding with a binder, which preferably is microporous alumina; further preferably, the pore size of the microporous alumina is 0.8-2.5 nm; with respect to 100 pbw amorphous silica-alumina particles, the amount of the binder is 3-20 pbw, preferably is 5-10 pbw.

In the method according to the present invention, there is no particular restriction on the conditions of drying and calcining involved in the catalyst preparation process; in other words, the conditions may be conventional conditions in the art respectively. Preferably, the conditions of the drying include: temperature of 80-150° C., time of 1-24 h; the conditions of the calcining include: temperature of 400-700° C., further preferably 450-600° C.; time of 1-24 h.

In the method according to the present invention, preferably, the molding of the catalyst is to process the catalyst into a spherical shape. There is no particular restriction on the molding method; in other words, any conventional molding method in the art may be used. For example, if the catalyst is to be processed into a spherical shape, an oil dropping method, rolling granulation method, or pellet molding method, etc., may be used; the geometric diameter of the spherical catalyst is 1-5 mm, preferably is 2-5 mm, optimally is 2-3 mm.

In the method according to the present invention, a molding promoter may be added in the molding process. There is no particular restriction on the selection and added amount of the molding promoter; in other words, the molding promoter and its added amount may be conventional molding promoter and added amount in the art. For example, the molding promoter may be sesbania powder or methyl cellulose, and the added amount may be 2-7 wt % of the catalyst to be molded.

In a third aspect, the present invention provides a catalyst prepared by the above-mentioned method. With that method, a novel catalyst in which silicon and tin are uniformly distributed in the shell can be prepared easily. The catalyst supports simultaneous MTBE cracking reaction and TBA dehydration reaction to prepare isobutylene, and achieves higher conversion rates of TBA (99.0% or higher) and MTBE (99.0% or higher), and higher selectivity for generating isobutylene (99.5% or higher).

In a fourth aspect, the present invention provides a use of the above-mentioned catalyst of the present invention in MTBE cracking reaction for preparing isobutylene and/or TBA dehydration reaction for preparing isobutylene.

In a fifth aspect, the present invention provides a method for preparing isobutylene, comprising: contacting the above-mentioned catalyst of the present invention with MTBE and/or TBA for reaction, to prepare isobutylene. Preferably, the catalyst contacts with a mixture of MTBE and TBA for reaction to prepare isobutylene, i.e., a MTBE cracking reaction for preparing isobutylene and a TBA dehydration reaction for preparing isobutylene may be executed simultaneously, under the catalyzing action of the catalyst.

In the method for preparing isobutylene according to the present invention, adding water can promote MTBE cracking; however, since the TBA dehydration reaction generates water in considerable quantity, the water may be utilized in the process. Therefore, water is not a 'must' in the mixture of MTBE and TBA, which is to say, the mixture of MTBE and TBA may contain water or doesn't contain water. To further promote MTBE cracking, preferably, contacting the catalyst with a mixture of MTBE and TBA that further contains 1-15 wt % water on the basis of the total weight of the mixture of MTBE and TBA, besides MTBE and TBA. The impurities in the mixture of MTBE and TBA may be essentially the same as the impurities contained in the conventional raw materials when MTBE is used as the raw material to prepare isobutylene and TBA is used as the raw material to prepare isobutylene by dehydration. Usually, on the basis of the total weight of the mixture of MTBE and TBA, the content of methyl sec-butyl ether is ≤0.2 wt %, the content of methanol is ≤0.05 wt %, the content of isobutylene oligomer is ≤10.05 wt %, and the content of C1-C4 hydrocarbons is ≤0.1 wt %.

In the method for preparing isobutylene according to the present invention, preferably, contacting the catalyst with a mixture of MTBE and TBA; in addition, the weight ratio of TBA to MTBE in the mixture of MTBE and TBA is 1:40-1:1, and the weight ratio of aluminum oxide containing silicon and tin to amorphous silica-alumina in the catalyst is 1:40-1:4; further preferably, the weight ratio of TBA to MTBE in the mixture of MTBE and TBA is 1:20-1:2, and the weight ratio of aluminum oxide containing silicon and tin to amorphous silica-alumina in the catalyst is 1:30-1:6.

The method for preparing isobutylene according to the present invention may be executed in an existing apparatus for MTBE cracking to prepare isobutylene or apparatus for TBA dehydration to prepare isobutylene. Preferably, the reaction conditions of the reaction of the mixture of MTBE and TBA catalyzed by the catalyst to prepare isobutylene include: total liquid hourly volumetric space velocity of $0.5\text{-}10^{-1}$, preferably $2\text{-}5^{-1}$; temperature of 190-260° C., preferably 200-230° C.; pressure of normal pressure to 0.6 MPa, further preferably normal pressure to 0.3 MPa. Those skilled in the art should appreciate that the pressure in the present invention is gauge pressure.

The method for preparing isobutylene according to the present invention may employ a fixed bed process or slurry bed process to prepare isobutylene, i.e., the reaction may be executed in a fixed bed-type reactor or slurry bed reactor.

If a slurry bed process is used, usually an inert solvent is required. A hydrocarbon liquid phase medium is a well-recognized inert solvent for slurry bed reaction. Further preferably, the method that employs a slurry bed process to prepare isobutylene comprises: mixing an inert solvent with the catalyst to prepare mixed slurry, and then loading the mixed slurry into a slurry bed reactor, wherein, the inert solvent is one or more of inert mineral oil, tail oil of hydrocracking, and liquid paraffinic hydrocarbon, and on the basis of the weight of the mixed slurry, the content of the catalyst is 3-40 wt %.

Examples

Hereunder the present invention will be detailed in some examples, but it should be noted that the present invention are not limited to those examples. In the following examples and comparative examples, unless otherwise specified, all of the raw materials are commercially available.

Wherein, the raw material purity and product composition are analyzed by gas chromatography. The specific surface area is measured with a cryogenic liquid nitrogen adsorption method as per the ASTM D3663-2003 standard.

The pore volume is measured with a cryogenic liquid nitrogen adsorption method as per the ASTM D4222-2003 standard.

The core-shell structure of the catalyst is ascertained with the following method: A JEM 2100 LaB6 high-resolution transmission electron microscope (TEM) from JEOL (a Japanese company) that has 0.23 nm resolution and is equipped with an X-ray energy dispersive spectrometer (EDX) from EDAX is used, the sample is grounded intensively in an agate mortar, and then is dispersed in absolute ethyl alcohol by ultrasonic dispersion for 20 min. 2-3 droplets of suspension liquid are dropped onto a micrograting carbon membrane supported by a copper screen; after the sample is dried, the sample is observed and analyzed by TEM observation, electron diffraction analysis, and elemental composition analysis.

Example 1

This example is provided here to describe the method for preparing the catalyst of the present invention, which is used to prepare isobutylene.

Amorphous silica-alumina powder FM1 (from Fushun Branch Company of SINOPEC Catalyst Co., Ltd., wherein, on the basis of the weight of the amorphous silica-alumina powder FM1, the content of silicon calculated in $SiO_2$ is 92.1 wt %, and the content of aluminum calculated in $Al_2O_3$ is 7.9 wt %; the specific surface area is 281 $m^2/g$, the pore volume is 0.58 mL/g, milled to particles in particle size of 200-400 mesh, i.e., about 30-80 μm) is immersed in 0.15 mol/L water solution of $Ni(NO_3)_2$ for 12 h, then the particles are calcined at 400° C. for 6 h, and then are processed in 300° C. saturated water vapor for 6 h; thus, amorphous silica-alumina powder FM1-1 with 0.61 wt % nickel oxide content (based on the weight of the amorphous silica-alumina powder FM1-1) is obtained. 10 wt % microporous alumina with average pore size equal to 1.5 nm is added as a binder into the amorphous silica-alumina powder FM1-1, the powder is molded by pellet molding into pellets with pellet size equal to 2.2-2.5 mm, and then the pellets are dried at 120° C. for 4h, and then are calcined at 400° C. for 6 h.

Aluminum hydroxide slurry LRJ1 is prepared with an aluminum isopropoxide hydrolysis method: water and aluminum isopropoxide are mixed at 120:1 molar ratio, the hydrolysis temperature is controlled at 80-85° C., and the aluminum isopropoxide is hydrolyzed for 1.5 h, and then is aged at 90-95° C. for 18 h; thus, aluminum hydroxide slurry LRJ1 with 21.3 wt % solid content is obtained; tin nitrate, tin octoate and dimethyl dichlorosilane are added slowly into the aluminum hydroxide slurry LRJ1 respectively while stirring, to obtain aluminum hydroxide slurry containing silicon and tin LRJ1-1, wherein, the added amount of tin nitrate and tin octoate calculated in tin is 0.38 wt % of the weight of pseudo-boehmite (aluminum hydroxide) calculated in aluminum oxide, and the molar ratio of tin nitrate to tin octoate is 1:1; the added amount of dimethyl dichlorosilane calculated in silicon is 1.23 wt % of the weight of the pseudo-boehmite (aluminum hydroxide) calculated in aluminum oxide.

The aluminum hydroxide slurry containing tin and silicon LRJ1-1 is sprayed on the molded pellets (the weight ratio of the aluminum oxide containing silicon and tin to the amorphous silica-alumina is 1:10), and then the pellets are dried at 120° C. for 4h and then calcined at 500° C. for 6 h; thus, a catalyst SL-1 is obtained.

Observed by TEM, the catalyst SL-1 has a core-shell structure, wherein, the size of the catalyst pellet is 2.2-2.5 mm, and the thickness of the shell is 20-25 μm; according to the result of statistics on 20 pellets sampled randomly, the average ratio of the radius of the core to the thickness of the shell is 100:2. Elemental analysis is carried out for the shell of the catalyst pellet, and the contents of silicon and tin elements are measured at 20 evenly dispersed points. The result is shown in Table 1. It is seen from the result: silicon and tin are uniformly distributed in the shell of the catalyst pellet, and the contents of silicon and tin essentially match the calculation results of their material inputs.

Example 2

This example is provided here to describe the method for preparing the catalyst of the present invention, which is used to prepare isobutylene.

7.5 wt % microporous alumina with average pore size equal to 1.5 nm and 2.0 wt % methyl cellulose are added as a binder and a molding promoter respectively into the amorphous silica-alumina powder FM1-1 obtained in the Example 1, the powder is molded by pellet molding into pellets with pellet size equal to 2.6-2.9 mm, and then the pellets are dried at 90° C. for 8h, and then are calcined at 650° C. for 3h.

Aluminum hydroxide slurry LRJ2 is prepared through a carbonization process by charging carbon dioxide gas into sodium metaaluminate solution: A $CO_2/N_2$ mixture that contains 30 wt % $CO_2$ is charged into sodium metaaluminate solution, a gelation reaction is executed at 30° C., and the pH at the end of the reaction is controlled to be 10.5-11.0; after the reaction is finished, aging, and the product of the reaction is washed with deionized water at 60° C. till the pH of the filtrate is 6.5; thus, aluminum hydroxide slurry LRJ2 with 31.2 wt % solid content is obtained. Tin tetrachloride and trimethylchlorosilane are added slowly into the aluminum hydroxide slurry LRJ2 respectively while stirring, to obtain aluminum hydroxide slurry containing silicon and tin LRJ2-1, wherein, the added amount of tin tetrachloride calculated in tin is 0.65 wt % of the weight of pseudo-boehmite (aluminum hydroxide) calculated in aluminum oxide, and the added amount of trimethylchlorosilane calculated in silicon is 0.85 wt % of the weight of the pseudo-boehmite (aluminum hydroxide) calculated in aluminum oxide.

The aluminum hydroxide slurry containing silicon and tin LRJ2-1 is sprayed on the molded pellets (the weight ratio of the aluminum oxide containing silicon and tin to the amorphous silica-alumina is 1:20), and then the pellets are dried at 90° C. for 8h and then calcined at 600° C. for 3 h; thus, a catalyst SL-2 is obtained.

Observed by TEM, the catalyst SL-2 has a core-shell structure, wherein, the size of the catalyst pellet is 2.6-2.9 mm, and the thickness of the shell is 50-56 μm; according to the result of statistics on 20 pellets sampled randomly, the average ratio of the radius of the core to the thickness of the shell is 100:4. Elemental analysis is carried out for the shell of the catalyst pellet, and the contents of silicon and tin elements are measured at 20 evenly dispersed points. The result is shown in Table 1. It is seen from the result: silicon and tin are uniformly distributed in the shell of the catalyst pellet, and the contents of silicon and tin essentially match the calculation results of their material inputs.

Example 3

This example is provided here to describe the method for preparing the catalyst of the present invention, which is used to prepare isobutylene.

Amorphous silica-alumina powder FM2 (from Fushun Branch Company of SINOPEC Catalyst Co., Ltd., wherein, on the basis of the weight of the amorphous silica-alumina powder FM2, the content of silicon calculated in $SiO_2$ is 82.2 wt %, and the content of aluminum calculated in $Al_2O_3$ is 17.8 wt %; the specific surface area is 335 $m^2/g$, the pore volume is 0.78 mL/g, milled to particles in particle size of 200-400 mesh, i.e., about 30-80 μm) is treated in saturated water vapor at 200° C. for 16 h, and then is immersed in 1.50 mol/L water solution of $Be(NO_3)_2$ for 12 h, then the particles are calcined at 500° C. for 5h; thus, amorphous silica-alumina powder FM2-1 with 1.02 wt % beryllium oxide content (based on the weight of the amorphous silica-alumina powder FM2-1) is obtained. 18 wt % microporous alumina with average pore size equal to 2.5 nm is added as a binder into the amorphous silica-alumina powder FM2-1, the powder is molded by pellet molding into pellets with pellet size equal to 2.2-2.5 mm, and then the pellets are dried at 120° C. for 4 h, and then are calcined at 400° C. for 6 h.

The aluminum hydroxide slurry containing tin and silicon LRJ1-1 obtained in the Example 1 is sprayed on the molded pellets (the weight ratio of the aluminum oxide containing silicon and tin to the amorphous silica-alumina is 1:25), and then the pellets are dried at 150° C. for 1.5 h and then calcined at 650° C. for 4 h; thus, a catalyst SL-3 is obtained.

Observed by TEM, the catalyst SL-3 has a core-shell structure, wherein, the size of the catalyst pellet is 2.2-2.5 mm, and the thickness of the shell is 52-60 μm; according to the result of statistics on 20 pellets sampled randomly, the average ratio of the radius of the core to the thickness of the shell is 100:5. Furthermore, elemental analysis is carried out for the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value <10% (the specific data is not shown). The result also indicates that silicon and tin are uniformly distributed in the shell of the catalyst pellet, and the contents of silicon and tin essentially match the calculation results of their material inputs.

Example 4

This example is provided here to describe the method for preparing the catalyst of the present invention, which is used to prepare isobutylene.

The aluminum hydroxide slurry containing tin and silicon LRJ2-1 obtained in the Example 2 is sprayed on the amorphous silica-alumina powder FM2-1 obtained in the Example 3 (the weight ratio of the aluminum oxide containing silicon and tin to the amorphous silica-alumina is 1:5), and then the powder is dried at 80° C. for 10 h and then calcined at 500° C. for 6 h; thus, catalyst powder is obtained. Then, 5 wt % microporous alumina with average pore size equal to 2.5 nm and 3.0 wt % sesbania powder are added as a binder and a molding promoter respectively into the catalyst powder, then powder is molded by pellet molding into catalyst pellets with pellet size equal to 2.4-2.7 mm, and then the pellets are dried at 120° C. for 4 h and then are calcined at 700° C. for 6 h; thus, a catalyst SL-4 is obtained.

Observed by TEM, the catalyst powder is in a form of pellets with pellet size equal to 40 μm-1 mm, and all of the pellets have a core-shell structure. The thickness of the shell is 5-8 μm; according to the result of statistics on 20 pellets sampled randomly, the average ratio of the radius of the core to the thickness of the shell is 100:10. Furthermore, elemental analysis is carried out for the shell of the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value ≤10% (the specific data is not shown). The result also indicates that silicon and tin are uniformly distributed in the shell of the catalyst pellet, and the contents of silicon and tin essentially match the calculation results of their material inputs.

Example 5

The method described in the Example 1 is used, but the amorphous silica-alumina powder FM1 is immersed in 0.15 mol/L water solution of $Ni(NO_3)_2$ for 12 h, and then the powder is calcined at 450° C. for 6 h, and then is treated in saturated water vapor at 150° C. for 20 h; thus, amorphous silica-alumina powder FM1-5 with 0.5 wt % nickel oxide content (based on the weight of the amorphous silica-alumina powder FM1-5) is obtained. 10 wt % microporous alumina with average pore size equal to 2.5 nm is added as a binder into the amorphous silica-alumina powder FM1-5, the powder is molded by pellet molding into pellets with pellet size equal to 2.2-2.5 mm, and then the pellets are dried at 100° C. for 5 h, and then are calcined at 600° C. for 4 h.

Tin dichloride, tin sulfate and phenyl chlorosilane are added slowly into the aluminum hydroxide slurry LRJ1 respectively while stirring, to obtain aluminum hydroxide slurry containing silicon and tin LRJ1-5, wherein, the added amount of tin dichloride and tin sulfate calculated in tin is 0.8 wt % of the weight of pseudo-boehmite (aluminum hydroxide) calculated in aluminum oxide, and the molar ratio of tin dichloride to tin sulfate is 1:1; the added amount of phenyl chlorosilane calculated in silicon is 1.5 wt % of the weight of the pseudo-boehmite (aluminum hydroxide) calculated in aluminum oxide.

The aluminum hydroxide slurry containing tin and silicon LRJ1-5 is sprayed on the molded pellets (the weight ratio of the aluminum oxide containing silicon and tin to the amorphous silica-alumina is 1:60), and then the pellets are dried at 100° C. for 5 h and then calcined at 600° C. for 4 h; thus, a catalyst SL-5 is obtained.

Observed by TEM, the catalyst SL-5 has a core-shell structure, wherein, the size of the catalyst pellet is 4.0-4.5 mm, and the thickness of the shell is 210-245 μm; according to the result of statistics on 20 pellets sampled randomly, the average ratio of the radius of the core to the thickness of the shell is 100:12. Furthermore, elemental analysis is carried out for the shell of the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value ≤10% (the specific data is not shown). The result also indicates that silicon and tin are uniformly distributed in the shell of the catalyst pellet, and the contents of silicon and tin essentially match the calculation results of their material inputs.

Example 6

The method described in the Example 1 is used, but the amorphous silica-alumina powder FM1 is immersed in 0.15 mol/L water solution of $Pd(NO_3)_2$ for 15 h, and then the powder is calcined at 600° C. for 4 h, and then is treated in saturated water vapor at 450° C. for 5 h; thus, amorphous silica-alumina powder FM1-6 with 1.5 wt % palladium oxide content (based on the weight of the amorphous silica-alumina powder FM1-6) is obtained. the amorphous silica-alumina powder FM1-6 is dried at 100° C. for 8 h and then calcined at 500° C. for 8 h; then, 10 wt % microporous alumina with average pore size equal to 2.5 nm is added as a binder into the amorphous silica-alumina powder FM1-6, the powder is molded by pellet molding into pellets with pellet size equal to 2.2-2.5 mm, and then the pellets are dried at 100° C. for 8 h, and then are calcined at 500° C. for 8 h.

Dibutyl tin dichloride and dimethyl dichlorosilane are added slowly into the aluminum hydroxide slurry LRJ1 respectively while stirring, to obtain aluminum hydroxide slurry containing silicon and tin LRJ1-6, wherein, the added amount of dibutyl tin dichloride calculated in tin is 1 wt % of the weight of pseudo-boehmite (aluminum hydroxide) calculated in aluminum oxide; the added amount of dimethyl dichlorosilane calculated in silicon is 2 wt % of the weight of the pseudo-boehmite (aluminum hydroxide) calculated in aluminum oxide.

The aluminum hydroxide slurry containing tin and silicon LRJ1-6 is sprayed on the molded pellets (the weight ratio of the aluminum oxide containing silicon and tin to the amorphous silica-alumina is 1:40), and then the pellets are dried at 120° C. for 4 h and then calcined at 400° C. for 16 h; thus, a catalyst SL-6 is obtained.

Observed by TEM, the catalyst SL-6 has a core-shell structure, wherein, the size of the catalyst pellet is 2.2-2.5 mm, and the thickness of the shell is 80-95 µm; according to the result of statistics on 20 pellets sampled randomly, the average ratio of the radius of the core to the thickness of the shell is 100:8. Furthermore, elemental analysis is carried out for the shell of the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value ≤10% (the specific data is not shown). The result also indicates that silicon and tin are uniformly distributed in the shell of the catalyst pellet, and the contents of silicon and tin essentially match the calculation results of their material inputs.

Example 7

The method described in the Example 1 is used, but the amorphous silica-alumina powder FM1 is immersed in 0.15 mol/L water solution of $Mg(NO_3)_2$ for 12 h, and then the powder is calcined at 400° C. for 6 h, and then is treated in saturated water vapor at 250° C. for 8 h; thus, amorphous silica-alumina powder FM1-7 with 1.5 wt % magnesium oxide content (based on the weight of the amorphous silica-alumina powder FM1-7) is obtained. 15 wt % microporous alumina with average pore size equal to 2.5 nm is added as a binder into the amorphous silica-alumina powder FM1-7, the powder is molded by pellet molding into catalyst pellets with pellet size equal to 2.2-2.5 mm, and then the pellets are dried at 120° C. for 4 h, and then are calcined at 400° C. for 6 h. Dibutyl tin dichloride and dimethyl dichlorosilane are added slowly into the aluminum hydroxide slurry LRJ1 respectively while stirring, to obtain aluminum hydroxide slurry containing silicon and tin LRJ1-7, wherein, the added amount of dibutyl tin dichloride calculated in tin is 1 wt % of the weight of pseudo-boehmite (aluminum hydroxide) calculated in aluminum oxide; the added amount of dimethyl dichlorosilane calculated in silicon is 0.5 wt % of the weight of the pseudo-boehmite (aluminum hydroxide) calculated in aluminum oxide.

The aluminum hydroxide slurry containing tin and silicon LRJ1-7 is sprayed on the molded pellets (the weight ratio of the aluminum oxide containing silicon and tin to the amorphous silica-alumina is 1:3), and then the pellets are dried at 120° C. for 4 h and then calcined at 650° C. for 4 h; thus, a catalyst SL-7 is obtained.

Observed by TEM, the catalyst SL-7 has a core-shell structure, wherein, the size of the catalyst pellet is 2.2-2.5 mm, and the thickness of the shell is 6-8 µm; according to the result of statistics on 20 pellets sampled randomly, the average ratio of the radius of the core to the thickness of the shell is 100:0.6. Furthermore, elemental analysis is carried out for the shell of the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value ≤10% (the specific data is not shown). The result also indicates that silicon and tin are uniformly distributed in the shell of the catalyst pellet, and the contents of silicon and tin essentially match the calculation results of their material inputs.

Example 8

The method described in the Example 1 is used, but no hydrothermal treatment of the amorphous silica-alumina is made after calcining when the amorphous silica-alumina powder FM1-1 is prepared. Thus, a catalyst SL-8 is obtained.

Observed by TEM, the catalyst SL-8 has a core-shell structure, wherein, the size of the catalyst pellet is 2.2-2.5 mm, and the thickness of the shell is 20-25 µm; according to the result of statistics on 20 pellets sampled randomly, the average ratio of the radius of the core to the thickness of the shell is 100:2. Furthermore, elemental analysis is carried out for the shell of the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value ≤10% (the specific data is not shown). The result also indicates that silicon and tin are uniformly distributed in the shell of the catalyst pellet, and the contents of silicon and tin essentially match the calculation results of their material inputs.

Example 9

The method described in the Example 1 is used, but the dimethyl dichlorosilane is replaced with polyether modified trisiloxane (model H-350 from Jiangxi Hito Chemical Co., Ltd.) in the same amount calculated in silicon when the aluminum hydroxide slurry containing silicon and tin LRJ1-1 is prepared. Thus, a catalyst SL-9 is obtained.

Observed by TEM, the catalyst SL-9 has a core-shell structure, wherein, the size of the catalyst pellet is 2.2-2.5 mm, and the thickness of the shell is 20-25 μm; according to the result of statistics on 20 pellets sampled randomly, the average ratio of the radius of the core to the thickness of the shell is 100:2. Furthermore, elemental analysis is carried out for the shell of the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value ≤10% (the specific data is not shown). The result also indicates that silicon and tin are uniformly distributed in the shell of the catalyst pellet, and the contents of silicon and tin essentially match the calculation results of their material inputs.

Example 10

The method described in the Example 1 is used, but the amorphous silica-alumina powder FM1 is treated in 300° C. saturated water vapor for 6 h, and the amorphous silica-alumina powder obtained through the hydrothermal treatment is used in replacement of the amorphous silica-alumina powder FM1-1 (i.e., the amorphous silica-alumina powder FM1-1 doesn't contain any activator). Thus, a catalyst SL-10 is obtained.

Observed by TEM, the catalyst SL-10 has a core-shell structure, wherein, the size of the catalyst pellet is 2.2-2.5 mm, and the thickness of the shell is 20-25 μm; according to the result of statistics on 20 pellets sampled randomly, the average ratio of the radius of the core to the thickness of the shell is 100:2. Furthermore, elemental analysis is carried out for the shell of the catalyst pellets, and the contents of silicon and tin elements are measured at 20 evenly dispersed points; the silicon content measured at each point meets (measured value−average value)/average value ≤5%, and the tin content measured at each point meets (measured value−average value)/average value ≤10% (the specific data is not shown). The result also indicates that silicon and tin are uniformly distributed in the shell of the catalyst pellet, and the contents of silicon and tin essentially match the calculation results of their material inputs.

Comparative Example 1

The method described in the Example 1 is used, but aluminum hydroxide slurry LRJ1 with 21.3 wt % solid content is sprayed onto the molded pellets (the weight ratio of the aluminum hydroxide calculated in aluminum oxide to the amorphous silica-alumina is 1:10), and then the pellets are dried at 120° C. for 4 h, and then are calcined at 500° C. for 6 h; thus, a catalyst DB-1 is obtained.

Comparative Example 2

The method described in the Example 1 is used, but the obtained aluminum hydroxide slurry containing silicon and tin LRJ1-1 is dried at 120° C. for 4 h, and then is calcined at 500° C. for 6 h; thus, aluminum oxide powder containing silicon and tin LRJ1-2 is obtained.

The amorphous silica-alumina powder FM1-1 in the Example 1 is mixed with the aluminum oxide powder containing silicon and tin LRJ1-2 at 10:1 weight ratio into a homogeneous state, and then 10 wt % microporous alumina with average pore size equal to 1.5 nm is added as a binder into the mixture, and the powder is molded by pellet molding into catalyst pellets with pellet size equal to 2.2-2.5 mm, then the pellets are dried at 120° C. for 4 h and then are calcined at 400° C. for 6 h; thus, a catalyst DB-2 is obtained.

Comparative Example 3

The method described in the Example 1 is used, but the aluminum hydroxide slurry LRJ1 in the Example 1 is dried at 120° C. for 4 h and then calcined at 500° C. for 6 h, and then 10 wt % microporous alumina with average pore size equal to 1.5 nm is added as a binder into the obtained powder, and the powder is molded by pellet molding into catalyst pellets with pellet size equal to 2.2-2.5 mm, then the pellets are dried at 120° C. for 4 h and then are calcined at 400° C. for 6 h; thus, a catalyst DB-3 is obtained.

Comparative Example 4

The method described in the Example 1 is used, but 10 wt % microporous alumina with average pore size equal to 1.5 nm is added as a binder into the aluminum oxide powder containing silicon and tin LRJ1-2 obtained in the Comparative Example 2, and the powder is molded by pellet molding into catalyst pellets with pellet size equal to 2.2-2.5 mm, then the pellets are dried at 120° C. for 4 h and then are calcined at 400° C. for 6 h; thus, a catalyst DB-4 is obtained.

Comparative Example 5

The method described in the Example 1 is used, but pellets with pellet size equal to 2.2-2.5 mm produced from the amorphous silica-alumina powder FM1-1 and the microporous alumina in the Example 1 are used as a catalyst DB-5.

Comparative Example 6

The method described in the Example 1 is used, but only dimethyl dichlorosilane is added into the aluminum hydroxide slurry LRJ1, without tin nitrate and tin octoate; the obtained aluminum hydroxide slurry that contains silicon is used in replacement of the aluminum hydroxide slurry containing silicon and tin LRJ1-1. Thus, a catalyst DB-6 is obtained.

Comparative Example 7

The method described in the Example 1 is used, but only tin nitrate and tin octoate are added into the aluminum hydroxide slurry LRJ1, without dimethyl dichlorosilane; the obtained aluminum hydroxide slurry that contains tin is used in replacement of the aluminum hydroxide slurry containing silicon and tin LRJ1-1. Thus, a catalyst DB-7 is obtained.

Comparative Example 8

The method described in the Example 1 is used, but magnesium nitrate is added instead of tin nitrate, tin octoate and dimethyl dichlorosilane into the aluminum hydroxide slurry LRJ1; the obtained aluminum hydroxide slurry that contains magnesium is used in replacement of the aluminum hydroxide slurry containing silicon and tin LRJ1-1. Thus, a catalyst DB-8 is obtained.

Comparative Example 9

The method described in the Example 2 is used, but the aluminum hydroxide slurry LRJ2 is sprayed onto molded pellets that are the same as the molded pellets in the Example 2 (the weight ratio of aluminum oxide to amorphous silica-alumina is the same as that in the Example 2), and then the pellets are dried at 90° C. for 8 h, and then are calcined at 600° C. for 3 h; thus, semi-finished catalyst pellets are obtained. Then, silicon and tin elements are loaded with an immersion method onto the surfaces of the semi-finished catalyst pellets, and the loaded amounts of silicon and tin elements are the same as those in the Example 2. Then, the pellets are dried at 90° C. for 8 h, and then are calcined at 600° C. for 3 h; thus, a catalyst DB-9 is obtained.

Examples 11-20

Isobutylene is prepared in a fixed bed-type reactor with the following methods: contacting the catalysts obtained in the Examples 1-10 (the methods for preparing isobutylene with the catalysts obtained in the Examples 1-10 correspond to the Examples 11-20 respectively) with a mixture of MTBE and TBA for reaction to prepare isobutylene. The conditions of the reaction, i.e., total liquid hourly volumetric space velocity (LHVSV), weight ratio of MTBE/TBA/water in the mixture of MTBE and TBA (i.e., LHVSV of MTBE/LHVSV of TBA/LHVSV of water), reaction temperature and reaction pressure, etc., and the results are shown in Table 2.

Wherein, the mixture of MTBE and TBA further contains impurities, in which, based on the total weight of the mixture of MTBE and TBA, the content of methyl sec-butyl ether is 0.1 wt %, the content of methanol is 0.02 wt %, the content of isobutylene oligomer is 0.03 wt %, and the content of C1-C4 hydrocarbons is 0.05 wt %.

Comparative Examples 10-18

Isobutylene is prepared with the method described in the Example 11, but the catalysts obtained in the Comparative Examples 1-9 are used to prepare isobutylene, and the isobutylene preparation methods correspond to the Comparative Examples 10-18 respectively; in addition, in the Comparative Examples 10-18, the conditions of the reaction, i.e., total LHVSV, weight ratio of MTBE/TBA/water (i.e., LHVSV of MTBE/LHVSV of TBA/LHVSV of water), reaction temperature and reaction pressure, etc., and the results are shown in Table 2.

TABLE 1

| Catalyst SL-1 | Si/Al$_2$O$_3$ (wt %) | Sn/Al$_2$O$_3$ (wt %) | Catalyst SL-2 | Si/Al$_2$O$_3$ (wt %) | Sn/Al$_2$O$_3$ (wt %) | Catalyst DB-9 | Si/Al$_2$O$_3$ (wt %) | Sn/Al$_2$O$_3$ (wt %) |
|---|---|---|---|---|---|---|---|---|
| A1 | 1.20 | 0.35 | A1 | 0.82 | 0.65 | A1 | 1.35 | 1.08 |
| A2 | 1.21 | 0.36 | A2 | 0.82 | 0.65 | A2 | 1.36 | 1.01 |
| A3 | 1.19 | 0.38 | A3 | 0.85 | 0.62 | A3 | 1.30 | 1.03 |
| A4 | 1.25 | 0.40 | A4 | 0.87 | 0.67 | A4 | 1.36 | 1.03 |
| A5 | 1.22 | 0.39 | A5 | 0.90 | 0.64 | A5 | 1.29 | 1.06 |
| A6 | 1.23 | 0.35 | A6 | 0.91 | 0.63 | A6 | 1.27 | 1.08 |
| A7 | 1.24 | 0.36 | A7 | 0.81 | 0.63 | A7 | 1.29 | 1.04 |
| A8 | 1.19 | 0.36 | A8 | 0.85 | 0.68 | A8 | 1.29 | 1.04 |
| A9 | 1.27 | 0.36 | A9 | 0.82 | 0.61 | A9 | 1.34 | 1.06 |
| A10 | 1.25 | 0.38 | A10 | 0.82 | 0.69 | A10 | 1.36 | 1.05 |
| B1 | 1.24 | 0.40 | B1 | 0.83 | 0.70 | B1 | 0.75 | 0.51 |
| B2 | 1.23 | 0.41 | B2 | 0.86 | 0.68 | B2 | 0.78 | 0.52 |
| B3 | 1.26 | 0.41 | B3 | 0.87 | 0.64 | B3 | 0.70 | 0.47 |
| B4 | 1.20 | 0.37 | B4 | 0.84 | 0.63 | B4 | 0.77 | 0.50 |
| B5 | 1.21 | 0.38 | B5 | 0.84 | 0.63 | B5 | 0.72 | 0.54 |
| C1 | 1.21 | 0.40 | C1 | 0.82 | 0.68 | C1 | 0.33 | 0.16 |
| C2 | 1.22 | 0.40 | C2 | 0.88 | 0.61 | C2 | 0.35 | 0.19 |
| C3 | 1.25 | 0.40 | C3 | 0.88 | 0.62 | C3 | 0.30 | 0.18 |
| C4 | 1.24 | 0.37 | C4 | 0.87 | 0.65 | C4 | 0.34 | 0.16 |
| C5 | 1.26 | 0.36 | C5 | 0.84 | 0.65 | C5 | 0.34 | 0.20 |
| Average value | 1.2285 | 0.3795 | Average value | 0.8500 | 0.6480 | Average value | — | — |
| Theoretical value | 1.23 | 0.38 | Theoretical value | 0.85 | 0.65 | Theoretical value | — | — |

Note:
The theoretical value is a value obtained by calculation according to the material input.

TABLE 2

| | Catalyst | Total LHSV, h$^{-1}$ | MTBE/TBA/Water (weight ratio) | Reaction temperature, ° C. | Reaction pressure, MPa | MTBE conversion rate, % | TBA conversion rate, % | Selectivity for isobutylene, % |
|---|---|---|---|---|---|---|---|---|
| Example 11 | SL-1 | 3 | 2/1/0 | 210 | 0.2 | 99.9 | 99.7 | 99.7 |
| Example 12-1 | SL-2 | 4 | 3/1/0 | 210 | 0.25 | 99.6 | 99.3 | 99.8 |
| Example 12-2 | SL-2 | 4.1 | 3/1/0.1 | 200 | 0.3 | 99.5 | 99.4 | 99.7 |
| Example 12-3 | SL-2 | 0.52 | 0.4/0.1/0.02 | 260 | Normal pressure | 99.9 | 99.9 | 99.9 |
| Example 13 | SL-3 | 6.5 | 6/0.5/0 | 210 | 0.6 | 99.5 | 99.4 | 99.7 |
| Example 14-1 | SL-4 | 3 | 2/1/0 | 210 | 0.2 | 99.4 | 99.4 | 99.7 |
| Example 14-2 | SL-4 | 1.7 | 1.5/0.2/0 | 230 | Normal pressure | 99.7 | 99.9 | 99.7 |

TABLE 2-continued

|  | Catalyst | Total LHSV, h$^{-1}$ | MTBE/ TBA/Water (weight ratio) | Reaction temperature, ° C. | Reaction pressure, MPa | MTBE conversion rate, % | TBA conversion rate, % | Selectivity for isobutylene, % |
|---|---|---|---|---|---|---|---|---|
| Example 14-3 | SL-4 | 10 | 7/3/0 | 190 | 0.6 | 99.3 | 99.3 | 99.8 |
| Example 15 | SL-5 | 3 | 2/1/0 | 210 | 0.2 | 99.5 | 99.3 | 99.7 |
| Example 16 | SL-6 | 3 | 2/1/0 | 210 | 0.2 | 99.1 | 99.5 | 99.8 |
| Example 17 | SL-7 | 3 | 2/1/0 | 210 | 0.2 | 99.2 | 99.3 | 99.6 |
| Example 18 | SL-8 | 3 | 2/1/0 | 210 | 0.2 | 99.0 | 99.1 | 99.5 |
| Example 19 | SL-9 | 3 | 2/1/0 | 210 | 0.2 | 99.4 | 99.1 | 99.6 |
| Example 20 | SL-10 | 3 | 2/1/0 | 210 | 0.2 | 99.1 | 99.1 | 99.5 |
| Comparative Example 10 | DB-1 | 3 | 2/1/0 | 210 | 0.2 | 97.0 | 92.0 | 99.3 |
| Comparative Example 11 | DB-2 | 3 | 2/1/0 | 210 | 0.2 | 98.8 | 94.0 | 99.3 |
| Comparative Example 12-1 | DB-3 | 1 | 0/1/0 | 210 | 0.2 | — | 91.8 | 92.5 |
| Comparative Example 12-2 | DB-3 | 1 | 0/1/0 | 265 | 0.2 | — | 97.2 | 93.5 |
| Comparative Example 13-1 | DB-4 | 1 | 0/1/0 | 210 | 0.2 | — | 93.4 | 84.3 |
| Comparative Example 13-2 | DB-4 | 1 | 0/1/0 | 265 | 0.2 | — | 98.5 | 83.8 |
| Comparative Example 14-1 | DB-5 | 2.6 | 2.5/0/0.1 | 210 | 0.2 | 93.6 | — | 99.2 |
| Comparative Example 14-2 | DB-5 | 2.6 | 2.5/0/0.1 | 230 | 0.2 | 98.2 | — | 99.3 |
| Comparative Example 15 | DB-6 | 3 | 2/1/0 | 210 | 0.2 | 85.3 | 91.7 | 98.2 |
| Comparative Example 16 | DB-7 | 3 | 2/1/0 | 210 | 0.2 | 97.0 | 92.3 | 93.3 |
| Comparative Example 17 | DB-8 | 3 | 2/1/0 | 210 | 0.2 | 92.0 | 91.0 | 88.3 |
| Comparative Example 18 | DB-9 | 4 | 3/1/0 | 210 | 0.25 | 98.6 | 88.2 | 92.1 |

It is seen from the comparison between the data of the Examples and the data of the Comparative Examples in the Table 2: with the catalyst of the present invention, which employs aluminum oxide containing silicon and tin as a shell and employs an amorphous silica-alumina particle and/or a particle aggregate as a core, utilizing the close cooperation between the shell and the core, a reaction process in which a MTBE cracking reaction and a TBA dehydration reaction happen simultaneously at a temperature of not higher than 260° C. to generate isobutylene is implemented, and higher conversion rates of TBA and MTBE and higher selectivity for isobutylene are achieved, wherein, the conversion rate of TBA is 99.0% or higher, the conversion rate of MTBE is 99.0% or higher, and the selectivity for isobutylene is 99.5% or higher.

It is seen from the comparison between the data of the Example 11 and the data of the Comparative Example 10 in the Table 2: with a catalyst that employs unmodified aluminum oxide as a shell, the conversion rates of MTBE and TBA are not high, and the selectivity for isobutylene is poor.

It is seen from the comparison between the data of the Example 11 and the data of the Comparative Example 11 in the Table 2: even with a catalyst prepared by mixing modified active aluminum oxide with amorphous silica-alumina (i.e., the catalyst is not in a core-shell structure), the results are not ideal, though the conversion rates of MTBE and TBA and the selectivity for isobutylene are improved to some degree.

It is seen from the comparison between the data of the Example 11 and the data of the Comparative Examples 12-1 and 12-2 in the Table 2: when an activated alumina catalyst is used in the TBA cracking reaction, though the catalyzing performance of the catalyst can be improved as the reaction temperature is increased (i.e., the catalyzing performance of the catalyst at 265° C. reaction temperature is much better than that at 210° C. reaction temperature), the conversion rate of TBA and the selectivity for isobutylene are not ideal when the temperature is increased to 265° C., and are still lower than the conversion rate of TBA and selectivity for isobutylene achieved with the catalyst of the present invention at 210° C.

It is seen from the comparison between the data of the Example 11 and the data of the Comparative Examples 13-1 and 13-2 in the Table 2: when an alumina catalyst modified by tin and silicon is used in the TBA cracking reaction, though the catalyzing performance of the catalyst can be improved as the reaction temperature is increased (i.e., the catalyzing performance of the catalyst at 265° C. reaction temperature is much better than that at 210° C. reaction temperature), the conversion rate of TBA and the selectivity for isobutylene are not ideal when the temperature is increased to 265° C., and are still lower than the conversion rate of TBA and selectivity for isobutylene achieved with the catalyst of the present invention at 210° C.

It is seen from the comparison between the data of the Example 11 and the data of the Comparative Examples 14-1 and 14-2 in the Table 2: when an amorphous silica-alumina catalyst is used in the MTBE cracking reaction, though the catalyzing performance of the catalyst can be improved as the reaction temperature is increased (i.e., the catalyzing performance of the catalyst at 230° C. reaction temperature is much better than that at 210° C. reaction temperature), the conversion rate of MTBE and the selectivity for isobutylene are not ideal when the temperature is increased to 230° C., and are still lower than the conversion rate of MTBE and selectivity for isobutylene achieved with the catalyst of the present invention at 210° C.

It is seen from the comparison between the data of the Example 11 and the data of the Comparative Examples 15-17 in the Table 2: when aluminum oxide containing silicon and tin is used as the shell of the catalyst of the present invention, the conversion rates of TBA and MTBE and the selectivity for isobutylene can be improved significantly.

It is seen from the comparison between the data of the Example 11 and the data of the Example 18 in the Table 2: if the amorphous silica-alumina is treated by hydrothermal treatment when the catalyst of the present invention is prepared, the conversion rates of TBA and MTBE and the selectivity for isobutylene can be further improved.

It is seen from the comparison between the data of the Example 11 and the data of the Example 19 in the Table 2: if chlorosilane is used as the silicon-containing compound to prepare the aluminum hydroxide slurry containing silicon and tin and they prepare the shell when the catalyst of the present invention is prepared, the conversion rates of TBA and MTBE and the selectivity for isobutylene can be further improved.

It is seen from the comparison between the data of the Example 11 and the data of the Example 20 in the Table 2: if the amorphous silica-alumina contains an activator when the catalyst of the present invention is prepared, the conversion rates of TBA and MTBE and the selectivity for isobutylene can be further improved.

While some preferred embodiments of the present invention are described above, the present invention is not limited to the details in those embodiments. Those skilled in the art can make modifications and variations to the technical scheme of the present invention, without departing from the spirit of the present invention. However, all these modifications and variations shall be deemed as falling into the protected scope of the present invention.

In addition, it should be noted that the specific technical features described in above embodiments can be combined in any appropriate form, provided that there is no conflict. To avoid unnecessary repetition, the possible combinations are not described specifically in the present invention.

Moreover, different embodiments of the present invention can be combined freely as required, as long as the combinations don't deviate from the ideal and spirit of the present invention. However, such combinations shall also be deemed as falling into the scope disclosed in the present invention.

The invention claimed is:

1. A catalyst having a core-shell structure, comprising:
   a core comprising an amorphous silica-alumina particle and/or a particle aggregate of a plurality of amorphous silica-alumina particles;
   a shell comprising aluminum oxide containing silicon and tin,
   wherein a weight ratio of the aluminum oxide containing silicon and tin to the amorphous silica-alumina is 1:60-1:3,
   wherein, in the aluminum oxide containing silicon and tin, on the basis of the weight of the aluminum oxide containing silicon and tin and calculated as elements, a content of silicon is 0.5-2 wt %, and a content of tin is 0.2-1 wt %, and
   wherein the amorphous silica-alumina has a specific surface area of 240-450 $m^2$/g and a pore volume of 0.4-0.9 mL/g.

2. The catalyst according to claim 1, wherein a ratio of a size of the core to a wall thickness of the shell is 200:0.5-200:20.

3. The catalyst according to claim 1, wherein the core is the amorphous silica-alumina particle and a wall thickness of the shell is 3-15 μm; or the core is the particle aggregate and a wall thickness of the shell is 5-300 μm.

4. The catalyst according to claim 1, wherein in the core, on the basis of the weight of the amorphous silica-alumina, a content of silicon calculated in $SiO_2$ is 60-99 wt %, and a content of aluminum calculated in $Al_2O_3$ is 1-40 wt %.

5. The catalyst according to claim 1, wherein the amorphous silica-alumina is obtained through hydrothermal treatment at a temperature of 150-450° C. for a duration of 5-24 h.

6. The catalyst according to claim 1, wherein the amorphous silica-alumina further comprises an activator that is one or more of Group IIA metal elements and Group VIII metal elements; wherein, in the activator-containing amorphous silica-alumina, on the basis of the weight of the activator-containing amorphous silica-alumina, a content of the activator calculated in oxide is 0.1-5 wt %.

7. The catalyst according to claim 6, wherein, on the basis of the weight of the activator-containing amorphous silica-alumina and the content of silicon calculated in $SiO_2$ is 60-99 wt %, the content of aluminum calculated in $Al_2O_3$ is 1-40 wt %.

8. The catalyst according to claim 1, further comprises a binder, wherein the binder is a microporous alumina having a pore size of 0.8-2.5 nm.

9. The catalyst according to claim 8, wherein, with respect to 100 pbw amorphous silica-alumina particles, a content of the binder is 3-20 pbw.

10. The catalyst according to claim 1, wherein a size of the catalyst is 1-5 mm.

11. A preparation method of a catalyst of claim 1, comprising:
    mixing a silicon-containing compound, a tin-containing compound, and an aluminum hydroxide slurry to obtain a modified aluminum hydroxide slurry containing silicon and tin; spraying the modified aluminum hydroxide slurry on amorphous silica-alumina particles and/or aggregates of amorphous silica-alumina particles, and drying and calcining to obtain the catalyst.

12. The method according to claim 11, wherein the silicon-containing compound, the tin-containing compound, and the aluminum hydroxide slurry are mixed by adding the silicon-containing compound and the tin-containing compound in batches or dropwise into the aluminum hydroxide slurry while stirring.

13. The method according to claim 11, wherein the amorphous silica-alumina is obtained through hydrothermal treatment at a temperature of 150-450° C. for a duration of 5-24h.

14. The method according to claim 11, wherein the amorphous silica-alumina further comprises an activator selected from one or more of Group IIA metal elements and Group VIII metal elements, and on the basis of the weight of the activator-containing amorphous silica-alumina, a content of the activator calculated in oxide is 0.1-5 wt%.

15. The method according to claim 14, wherein the Group IIA metal elements are one or more of Be, Mg and Ca, and the Group VIII metal elements are one or more of Ni, Pd and Pt.

16. The method according to claim 11, wherein the silicon-containing compound is one or more of chlorosilane and polyether modified silicon oil, the chlorosilane is one or more of dimethyl dichlorosilane, trimethylchlorosilane, and phenyl chlorosilane; the tin-containing compound is one or more of tin dichloride, tin tetrachloride, tin nitrate, tin sulfate, tin octoate, and dibutyl tin dichloride.

17. The method according to claim 11, further comprising molding a resulting material from the spraying step.

18. The method according to claim 11, wherein the particle aggregates are obtained by molding amorphous silica-alumina particles.

19. The method according to claim 17, wherein the molding is carried out by bonding with a binder, wherein the binder is a microporous alumina having a pore size of 0.8-2.5 nm, and, with respect to 100 pbw amorphous silica-alumina particles, an amount of the binder is 3-20 pbw.

20. The method according to claim 18, wherein the molding is carried out by bonding with a binder, wherein the binder is a microporous alumina having a pore size of 0.8-2.5 nm, and, with respect to 100 pbw amorphous silica-alumina particles, an amount of the binder is 3-20 pbw.

21. A method for preparing isobutylene, comprising: contacting the catalyst according to claim 1 with a reactant comprising MTBE and/or TBA under reaction conditions in a reactor to produce isobutylene.

22. The method according to claim 21, wherein the reactant comprises MTBE, TBA, and water, and, on the basis of the total weight of the reactant a content of water is 1-15 wt%.

23. The method according to claim 21, wherein the reactant further comprises, on the basis of the total weight of the mixture, methyl sec-butyl ether of less than or equal to 0.2 wt%, methanol of less than or equal to 0.05 wt%, isobutylene oligomer of less than or equal to 0.05 wt%, and C1-C4 hydrocarbons of less than or equal to 0.1 wt%.

24. The method according to claim 21, wherein the reaction conditions comprise a total liquid hourly volumetric space velocity of $0.5-10h^{-1}$, a temperature of 190-260° C. and a pressure of normal pressure to 0.6 MPa.

25. The method according to claim 21, wherein the reactor is a fixed bed-type reactor or a slurry bed reactor.

26. The catalyst according to claim 6, wherein the Group IIA metal elements are one or more of Be, Mg and Ca, and the Group VIII metal elements are one or more of Ni, Pd and Pt.

* * * * *